United States Patent
Montag et al.

(12) 
(10) Patent No.: US 12,350,073 B2
(45) Date of Patent: Jul. 8, 2025

(54) SIGNAL AND CORRECTION PROCESSING FOR ANATOMICAL STRUCTURE MAPPING DATA

(71) Applicant: BIOSENSE WEBSTER (ISRAEL) LTD., Yokneam (IL)

(72) Inventors: Avram Dan Montag, Haifa (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 255 days.

(21) Appl. No.: 17/116,854

(22) Filed: Dec. 9, 2020

(65) Prior Publication Data

US 2022/0175323 A1    Jun. 9, 2022

(51) Int. Cl.
| | | |
|---|---|---|
| *A61B 5/00* | (2006.01) | |
| *A61B 5/287* | (2021.01) | |
| *A61B 5/346* | (2021.01) | |
| *G16H 50/20* | (2018.01) | |
| *G16H 50/50* | (2018.01) | |

(52) U.S. Cl.
CPC ............ *A61B 5/7264* (2013.01); *A61B 5/287* (2021.01); *A61B 5/346* (2021.01); *A61B 5/6852* (2013.01); *A61B 5/6885* (2013.01); *G16H 50/20* (2018.01); *G16H 50/50* (2018.01); *A61B 2562/0257* (2013.01)

(58) Field of Classification Search
CPC ....... A61B 5/0538; A61B 5/287; A61B 5/346; A61B 5/349; A61B 5/367; A61B 5/6844; A61B 5/6852; A61B 5/7264; A61B 2562/0257; G16H 50/20; G16H 50/50; H04N 21/25891

See application file for complete search history.

(56) References Cited

U.S. PATENT DOCUMENTS

| | | | |
|---|---|---|---|
| 5,755,664 A | 5/1998 | Rubenstein | |
| 6,301,496 B1 | 10/2001 | Reisfeld | |
| 9,050,011 B2 | 6/2015 | Rubenstein et al. | |
| 2004/0153128 A1 | 8/2004 | Suresh et al. | |
| 2011/0144510 A1* | 6/2011 | Ryu ..................... | A61B 5/1107 600/509 |
| 2011/0158496 A1 | 6/2011 | Ciofolo-Veit et al. | |

(Continued)

OTHER PUBLICATIONS

Anter, E, et al. Activation mapping with integration of vector and velocity information improves the ability to identify the mechanism and location of complex scar-related atrial tachycardias. Circ Arrhythm Electrophysiol. 2018;11:e006536. DOI: 10.1161/CIRCEP.118. 006536 (Year: 2018).*

(Continued)

*Primary Examiner* — Jennifer Pitrak McDonald
*Assistant Examiner* — Shreya Anjaria
(74) *Attorney, Agent, or Firm* — Volpe Koenig

(57) ABSTRACT

A method is provided. The method is implemented by a mapping engine. The method includes receiving biometric data of at least a portion of an anatomical structure from at least a catheter and analyzing the biometric data based on an automatic tagging operation, a time weighted local activation time assignment operation, or a discrimination operation. The method also includes determining scar tissue of the portion of the anatomical structure based on the analyzing of the biometric data.

15 Claims, 10 Drawing Sheets

(56) References Cited

U.S. PATENT DOCUMENTS

| | | | | |
|---|---|---|---|---|
| 2012/0184865 A1* | 7/2012 | Harlev | ............... | A61B 5/283 600/509 |
| 2014/0081114 A1* | 3/2014 | Shachar | ............... | A61B 5/24 600/378 |
| 2015/0157233 A1* | 6/2015 | Grenz | ............... | A61N 1/3702 607/9 |
| 2016/0022375 A1* | 1/2016 | Blake | ............... | A61B 34/10 600/424 |
| 2017/0185740 A1 | 6/2017 | Seegerer et al. | | |
| 2020/0146579 A1 | 5/2020 | Bar-Tal et al. | | |

OTHER PUBLICATIONS

Zahra, Binish & Athar, Atifa & Khan, Muhammad & Abbas, Sagheer & Ahmad, Gulzar. (2019). Automated diagnosis of liver disorder using multilayer neuro-fuzzy. International Journal of Advanced and Applied Sciences. 6. 23-32. 10.21833/ijaas.2019.02.005. (Year: 2019).*

European Search Report for corresponding EPA No. 21213005.8 dated May 25, 2022.

* cited by examiner

SIGNAL AND CORRECTION PROCESSING FOR ANATOMICAL STRUCTURE MAPPING DATA

FIELD OF INVENTION

The present invention is related to signal processing. More particularly, the present invention relates to signal and correction processing for anatomical structure mapping data.

BACKGROUND

In medical procedures, such as mapping electrical activity of an anatomical structure (e.g., an organ, such as a heart), it is important to accurately identify non-conducting tissue (e.g., scar tissue). However, current coherent mapping algorithms require user intervention for scar tissue identification (e.g., manual tagging of signals attributed to scar tissue).

For instance, as discussed in U.S. Application No. 2020/0146579, which is incorporated herein by reference, current coherent mapping algorithms for a heart indicate correspondences between a set of local activation times (LATs) and a group of spatial map elements when mapping electrical activity of the heart. LATs are indications of a flow of electrical activity through walls of the heart, associated with a beating of the heart. The spatial map elements (e.g., such as triangles) may be generated from measured positions of the heart wall. Note that current coherent mapping algorithms can show correspondences between the LATs and the triangles in a mesh form, superimposed on a graphic representation of the wall of the heart, as the mapping. To refine this mesh form and mapping, current coherent mapping algorithms perform interpolations with respect to the mesh form imposed on the wall of the heart and by calculation of velocity vectors for an electrical wave on the mesh form (e.g., for each triangle, a signal arrival time and a signal velocity vector is calculated). Yet, despite indicating correspondences and performing these interpolation operations, current coherent mapping algorithms still require manual tagging of scar associated signals.

SUMMARY

According to an embodiment, a method is provided. The method is implemented by a mapping engine. The method includes receiving biometric data of at least a portion of an anatomical structure from at least a catheter and analyzing the biometric data based on an automatic tagging operation, a time weighted local activation time assignment operation, or a discrimination operation. The method also includes determining scar tissue of the portion of the anatomical structure based on the analyzing of the biometric data.

According to one or more embodiments, the method embodiment above can be implemented as an apparatus, a system, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Disclosed herein is a signal processing system and method. More particularly, the present invention relates to signal and correction processing for anatomical structure mapping data. The signal and correction processing is a processor executable code or software that is necessarily rooted in process operations by, and in processing hardware of, medical device equipment. For ease of explanation, the signal and correction processing is described herein with respect to mapping a heart; however, any anatomical structure, body part, organ, or portion thereof can be a target for mapping by the signal and correction processing described herein. According to an exemplary embodiment, the signal and correction processing is implemented by a mapping engine.

As an overview, the mapping engine generates a map of a heart by performing interpolation operations using biometric data from a catheter. The mapping engine, generally, ensures that all electrical signals (e.g., the biometric data) from the catheter that are used in the interpolation operations to create the map of the heart are correctly associated with a reference time associated with a heartbeat. To achieve this aim, the mapping engine automatically identifies scar tissue on the heart from the electrical signals (e.g., using the notion that scar tissue blocks the heartbeat by more or less not conducting electrical signals). More particularly, the mapping engine provides a number of operations for assigning scar probabilities (e.g., identify scar tissue) to the electrical signals (e.g., measurements or annotation points) of the tissue of the heart detected by the catheter when those electrical signals include an indication of tissue contact (e.g., at a certain time) and a low or no voltage (e.g., slow or non-conduction conditions). That is to say, the mapping engine can determine whether an annotation point of the map contributes to scar tissue on a nearby surface of the heart. Further, the mapping engine can determine whether the annotation point falls within one of three categories: normal conductivity, low conductivity, and no conductivity.

According to an exemplary embodiment, the mapping engine analyzes biometric data based on at least one of an automatic tagging operation, a time weighted LAT assignment operation, and a discrimination operation to determine scar tissue of a heart. In this way, mapping engine presents advances in the determination of scar probability values. The technical effects and benefits of the mapping engine include reducing user intervention, improving scar identification, and enabling discrimination between low conduction and no conduction (e.g., no manual tagging). Thus, the mapping engine particularly utilizes and transforms medical device equipment to enable/implement signal and correction processing that are otherwise not currently available or currently performed by current coherent mapping algorithms.

Figure 1:
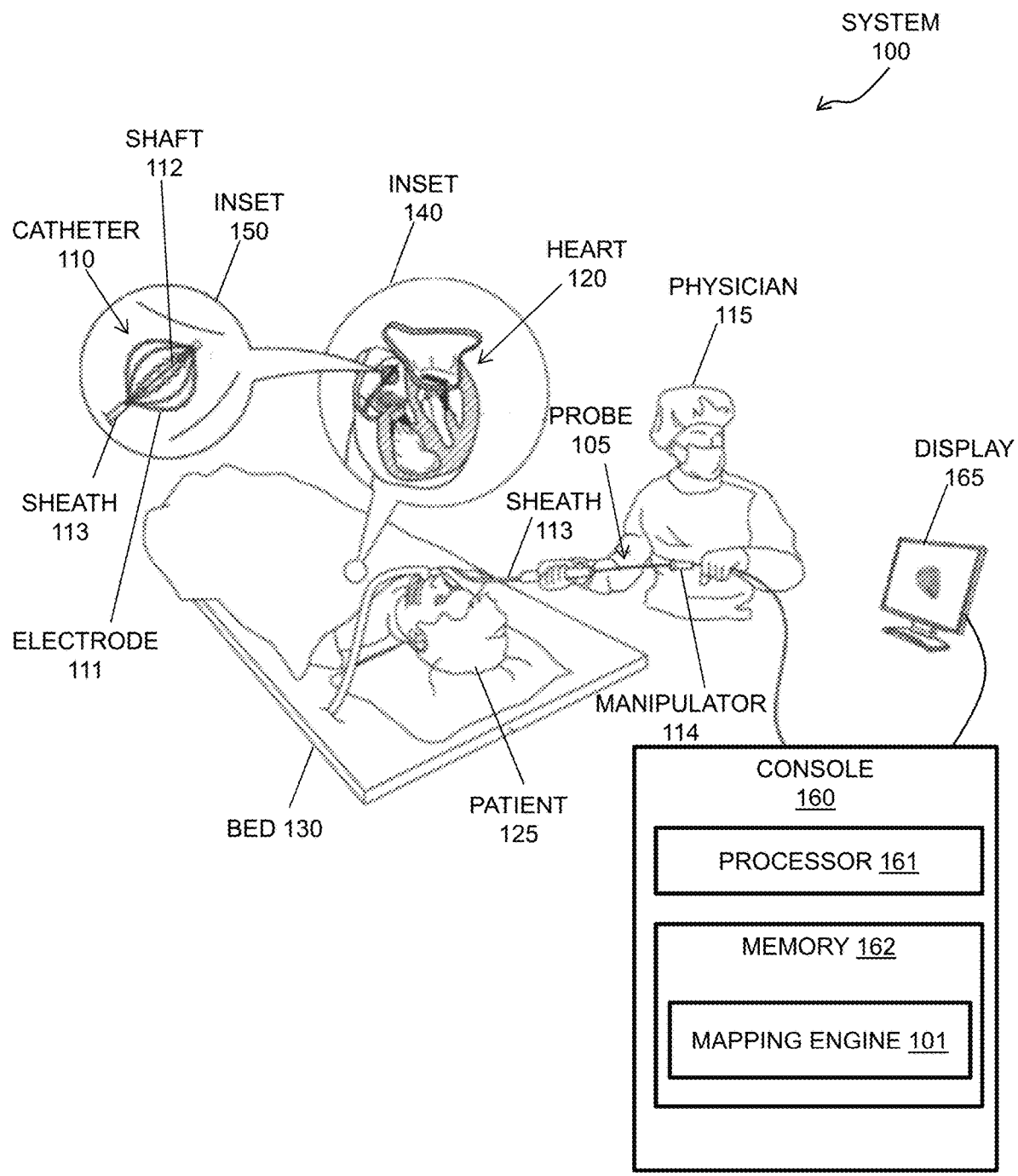
FIG. 1 illustrates a diagram of an exemplary system in which one or more features of the disclosure subject matter can be implemented according to one or more embodiments.

FIG. 1 is a diagram of a system 100 (e.g., medical device equipment) in which one or more features of the subject matter herein can be implemented according to one or more embodiments. All or part of the system 100 can be used to collect information (e.g., biometric data and/or a training dataset) and/or used to implement a signal and correction processing (e.g., a mapping engine 101 for signal and correction processing for anatomical structure mapping data) as described herein. The system 100, as illustrated, includes a probe 105 with a catheter 110 (including at least one electrode 111), a shaft 112, a sheath 113, and a manipulator 114. The system 100, as illustrated, also includes a physician 115 (or a medical professional or clinician), a heart 120, a patient 125, and a bed 130 (or a table). Note that insets 140 and 150 show the heart 120 and the catheter 110 in greater detail. The system 100 also, as illustrated, includes a console 160 (including one or more processors 161 and memories 162) and a display 165. Note further each element and/or item of the system 100 is representative of one or more of that element and/or that item. The example of the system 100 shown in FIG. 1 can be modified to implement the embodiments disclosed herein. The disclosed embodiments can similarly be applied using other system components and settings. Additionally, the system 100 can include additional components, such as elements for sensing electrical activity, wired or wireless connectors, processing and display devices, or the like.

The system 100 can be utilized to detect, diagnose, and/or treat cardiac conditions (e.g., using the mapping engine 101). Cardiac conditions, such as cardiac arrhythmias, persist as common and dangerous medical ailments, especially in the aging population. For instance, the system 100 can be part of a surgical system (e.g., CARTO® system sold by Biosense Webster) that is configured to obtain biometric data (e.g., anatomical and electrical measurements of a patient's anatomical structure or organ, such as the heart 120) and perform a cardiac ablation procedure. More particularly, treatments for cardiac conditions such as cardiac arrhythmia often require obtaining a detailed mapping of cardiac tissue, chambers, veins, arteries and/or electrical pathways. For example, a prerequisite for performing a catheter ablation (as described herein) successfully is that the cause of the cardiac arrhythmia is accurately located in a chamber of the heart 120. Such locating may be done via an electrophysiological investigation during which electrical potentials are detected spatially resolved with a mapping catheter (e.g., the catheter 110) introduced into the chamber of the heart 120. This electrophysiological investigation, the so-called electro-anatomical mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time. In this case, the mapping engine 101 can be directly stored and executed by the catheter 110.

In patients (e.g., the patient 125) with normal sinus rhythm (NSR), the heart (e.g., the heart 120), which includes atrial, ventricular, and excitatory conduction tissue, is electrically excited to beat in a synchronous, patterned fashion. Note that this electrical excitement can be detected as intracardiac electrocardiogram (IC ECG) data or the like.

In patients (e.g., the patient 125) with a cardiac arrhythmia (e.g., atrial fibrillation or aFib), abnormal regions of cardiac tissue do not follow a synchronous beating cycle associated with normally conductive tissue, which is in contrast to patients with NSR. Instead, the abnormal regions of cardiac tissue aberrantly conduct to adjacent tissue, thereby disrupting the cardiac cycle into an asynchronous cardiac rhythm. Note that this asynchronous cardiac rhythm can also be detected as the IC ECG data. Such abnormal conduction has been previously known to occur at various regions of the heart 120, for example, in the region of the sino-atrial (SA) node, along the conduction pathways of the atrioventricular (AV) node, or in the cardiac muscle tissue forming the walls of the ventricular and atrial cardiac chambers. There are other conditions, such as flutter, where the pattern of abnormally conducting tissues lead to reentry paths such that the chamber beats in a regular pattern that can be multiple times the sinus rhythm.

In support of the system 100 detecting, diagnosing, and/or treating cardiac conditions, the probe 105 can be navigated by the physician 115 into the heart 120 of the patient 125 lying on the bed 130. For instance, the physician 115 can insert the shaft 112 through the sheath 113, while manipulating a distal end of the shaft 112 using the manipulator 114 near the proximal end of the catheter 110 and/or deflection from the sheath 113. As shown in an inset 140, the catheter 110 can be fitted at the distal end of the shaft 112. The catheter 110 can be inserted through the sheath 113 in a collapsed state and can be then expanded within the heart 120.

Generally, electrical activity at a point in the heart 120 may be typically measured by advancing the catheter 110 containing an electrical sensor at or near its distal tip (e.g., the at least one electrode 111) to that point in the heart 120, contacting the tissue with the sensor and acquiring data at that point. One drawback with mapping a cardiac chamber using a catheter type containing only a single, distal tip electrode is the long period of time required to accumulate data on a point-by-point basis over the requisite number of points required for a detailed map of the chamber as a whole. Accordingly, multiple-electrode catheters (e.g., the catheter 110) have been developed to simultaneously measure electrical activity at multiple points in the heart chamber.

The catheter 110, which can include the at least one electrode 111 and a catheter needle coupled onto a body thereof, can be configured to obtain biometric data, such as electrical signals of an intra-body anatomical structure (e.g., the heart 120), and/or to ablate tissue areas of thereof (e.g., a cardiac chamber of the heart 120). Note that the electrodes 111 are representative of any like elements, such as tracking coils, piezoelectric transducer, electrodes, or combination of elements configured to ablate the tissue areas or to obtain the biometric data. According to one or more embodiments, the catheter 110 can include one or more position sensors that used are to determine trajectory information. The trajectory information can be used to infer motion characteristics, such as the contractility of the tissue.

Biometric data (e.g., patient biometrics, patient data, or patient biometric data) can include one or more of local activation times (LATs), electrical activity, topology, bipolar mapping, reference activity, ventricle activity, dominant frequency, impedance, or the like. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts. A dominant frequency can be a frequency or a range of frequency that is prevalent at a portion of a body part and can be different in different portions of the same body part. For example, the dominant frequency of a PV of a heart can be different than the dominant frequency of the right atrium of the same heart. Impedance can be the resistance measurement at a given area of a body part.

Examples of biometric data include, but are not limited to, patient identification data, IC ECG data, bipolar intracardiac reference signals, anatomical and electrical measurements, trajectory information, body surface (BS) ECG data, historical data, brain biometrics, blood pressure data, ultrasound signals, radio signals, audio signals, a two- or three-dimensional image data, blood glucose data, and temperature data. The biometrics data can be used, generally, to monitor, diagnosis, and treatment any number of various diseases, such as cardiovascular diseases (e.g., arrhythmias, cardiomyopathy, and coronary artery disease) and autoimmune diseases (e.g., type I and type II diabetes). Note that BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

For example, the catheter 110 can use the electrodes 111 to implement intravascular ultrasound and/or MRI catheterization to image the heart 120 (e.g., obtain and process the biometric data). Inset 150 shows the catheter 110 in an enlarged view, inside a cardiac chamber of the heart 120. Although the catheter 110 is shown to be a point catheter, it will be understood that any shape that includes one or more electrodes 111 can be used to implement the embodiments disclosed herein.

Examples of the catheter 110 include, but are not limited to, a linear catheter with multiple electrodes, a balloon catheter including electrodes dispersed on multiple spines that shape the balloon, a lasso or loop catheter with multiple electrodes, or any other applicable shape. Linear catheters can be fully or partially elastic such that it can twist, bend, and or otherwise change its shape based on received signal and/or based on application of an external force (e.g., cardiac tissue) on the linear catheter. The balloon catheter can be designed such that when deployed into a patient's body, its electrodes can be held in intimate contact against an endocardial surface. As an example, a balloon catheter can be inserted into a lumen, such as a pulmonary vein (PV). The balloon catheter can be inserted into the PV in a deflated state, such that the balloon catheter does not occupy its maximum volume while being inserted into the PV. The balloon catheter can expand while inside the PV, such that those electrodes on the balloon catheter are in contact with an entire circular section of the PV. Such contact with an entire circular section of the PV, or any other lumen, can enable efficient imaging and/or ablation.

According to other examples, body patches and/or body surface electrodes may also be positioned on or proximate to a body of the patient 125. The catheter 110 with the one or more electrodes 111 can be positioned within the body (e.g., within the heart 120) and a position of the catheter 110 can be determined by the 100 system based on signals transmitted and received between the one or more electrodes 111 of the catheter 110 and the body patches and/or body surface electrodes. Additionally, the electrodes 111 can sense the biometric data from within the body of the patient 125, such as within the heart 120 (e.g., the electrodes 111 sense the electrical potential of the tissue in real time). The biometric data can be associated with the determined position of the catheter 110 such that a rendering of the patient's body part (e.g., the heart 120) can be displayed and show the biometric data overlaid on a shape of the body part.

The probe 105 and other items of the system 100 can be connected to the console 160. The console 160 can include any computing device, which employs the signal and correction processing (represented as the mapping engine 101). According to an embodiment, the console 160 includes the one or more processors 161 (any computing hardware) and the memory 162 (any non-transitory tangible media), where the one or more processors 161 execute computer instructions with respect the mapping engine 101 and the memory 162 stores these instructions for execution by the one or more processors 161. For instance, the console 160 can be configured to receive and process the biometric data and determine if a given tissue area conducts electricity. In some embodiments, the console 160 can be further programmed by the mapping engine 101 (in software) to carry out the functions of receiving biometric data of at least a portion of an anatomical structure from at least a catheter, analyzing the biometric data based on an automatic tagging operation, a time weighted local activation time assignment operation, or a discrimination operation, and determining scar tissue of the portion of the anatomical structure based on the analyzing of the biometric data. According to one or more embodiments, the mapping engine 101 can be external to the console 160 and can be located, for example, in the catheter 110, in an external device, in a mobile device, in a cloud-based device, or can be a standalone processor. In this regard, the mapping engine 101 can be transferable/downloaded in electronic form, over a network.

In an example, the console 160 can be any computing device, as noted herein, including software (e.g., the mapping engine 101) and/or hardware (e.g., the processor 161 and the memory 162), such as a general-purpose computer, with suitable front end and interface circuits for transmitting and receiving signals to and from the probe 105, as well as for controlling the other components of the system 100. For example, the front end and interface circuits include input/output (I/O) communication interfaces that enables the console 160 to receive signals from and/or transfer signals to the at least one electrode 111. The console 160 can include real-time noise reduction circuitry typically configured as a field programmable gate array (FPGA), followed by an analog-to-digital (A/D) ECG or electrocardiograph/electromyogram (EMG) signal conversion integrated circuit. The console 160 can pass the signal from an A/D ECG or EMG circuit to another processor and/or can be programmed to perform one or more functions disclosed herein.

The display 165, which can be any electronic device for the visual presentation of the biometric data, is connected to the console 160. According to an embodiment, during a procedure, the console 160 can facilitate on the display 165 a presentation of a body part rendering to the physician 115 and store data representing the body part rendering in the memory 162. For instance, maps depicting motion characteristics can be rendered/constructed based on the trajectory information sampled at a sufficient number of points in the heart 120. As an example, the display 165 can include a touchscreen that can be configured to accept inputs from the medical professional 115, in addition to presenting the body part rendering.

In some embodiments, the physician 115 can manipulate the elements of the system 100 and/or the body part rendering using one or more input devices, such as a touch pad, a mouse, a keyboard, a gesture recognition apparatus, or the like. For example, an input device can be used to change a position of the catheter 110, such that rendering is updated. Note that the display 165 can be located at a same location or a remote location, such as a separate hospital or in separate healthcare provider networks.

According to one or more embodiments, the system 100 can also obtain the biometric data using ultrasound, computed tomography (CT), MRI, or other medical imaging techniques utilizing the catheter 110 or other medical equipment. For instance, the system 100 can obtain ECG data and/or anatomical and electrical measurements of the heart 120 (e.g., the biometric data) using one or more catheters 110 or other sensors. More particularly, the console 160 can be connected, by a cable, to BS electrodes, which include adhesive skin patches affixed to the patient 125. The BS electrodes can procure/generate the biometric data in the form of the BS ECG data. For instance, the processor 161 can determine position coordinates of the catheter 110 inside the body part (e.g., the heart 120) of the patient 125. The position coordinates may be based on impedances or electromagnetic fields measured between the body surface electrodes and the electrode 111 of the catheter 110 or other electromagnetic components. Additionally, or alternatively, location pads, which generate magnetic fields used for navigation, may be located on a surface of the bed 130 and may be separate from the bed 130. The biometric data can be transmitted to the console 160 and stored in the memory 162. Alternatively, or in addition, the biometric data may be transmitted to a server, which may be local or remote, using a network as further described herein.

According to one or more embodiments, the catheter 110 may be configured to ablate tissue areas of a cardiac chamber of the heart 120. Inset 150 shows the catheter 110 in an enlarged view, inside a cardiac chamber of the heart 120. For instance, ablation electrodes, such as the at least one electrode 111, may be configured to provide energy to tissue areas of an intra-body anatomical structure (e.g., the heart 120). The energy may be thermal energy and may cause damage to the tissue area starting from the surface of the tissue area and extending into the thickness of the tissue area. The biometric data with respect to ablation procedures (e.g., ablation tissues, ablation locations, etc.) can be considered ablation data.

According to an example, with respect to obtaining the biometric data, a multi-electrode catheter (e.g., the catheter 110) can be advanced into a chamber of the heart 120. Anteroposterior (AP) and lateral fluorograms can be obtained to establish the position and orientation of each of the electrodes. ECGs can be recorded from each of the electrodes 111 in contact with a cardiac surface relative to a temporal reference, such as the onset of the P-wave in sinus rhythm from a BS ECG and/or the related to the signals from electrodes 111 of the catheter 110 placed in the coronary sinus. The system, as further disclosed herein, may differentiate between those electrodes that register electrical activity and those that do not due to absence of close proximity to the endocardial wall. After initial ECGs are recorded, the catheter may be repositioned, and fluorograms and ECGs may be recorded again. An electrical map (e.g., via cardiac mapping) can then be constructed from iterations of the process above.

Cardiac mapping can be implemented using one or more techniques. Generally, mapping of cardiac areas such as cardiac regions, tissue, veins, arteries and/or electrical pathways of the heart 120 may result in identifying problem areas such as scar tissue, arrhythmia sources (e.g., electric rotors), healthy areas, and the like. Cardiac areas may be mapped such that a visual rendering of the mapped cardiac areas is provided using a display, as further disclosed herein. Additionally, cardiac mapping (which is an example of heart imaging) may include mapping based on one or more modalities such as, but not limited to local activation time (LAT), local activation velocity, an electrical activity, a topology, a bipolar mapping, a dominant frequency, or an impedance. Data (e.g., biometric data) corresponding to multiple modalities may be captured using a catheter (e.g., the catheter 110) inserted into a patient's body and may be provided for rendering at the same time or at different times based on corresponding settings and/or preferences of the physician 115.

As an example of a first technique, cardiac mapping may be implemented by sensing an electrical property of heart tissue, for example, LAT, as a function of the precise location within the heart 120. The corresponding data (e.g., biometric data) may be acquired with one or more catheters (e.g., the catheter 110) that are advanced into the heart 1120 and that have electrical and location sensors (e.g., the electrodes 111) in their distal tips. As specific examples, location and electrical activity may be initially measured on about 10 to about 20 points on the interior surface of the heart 120. These data points may be generally sufficient to generate a preliminary reconstruction or map of the cardiac surface to a satisfactory quality. The preliminary map may be combined with data taken at additional points to generate a more comprehensive map of the heart's electrical activity. In clinical settings, it is not uncommon to accumulate data at 100 or more sites (e.g., several thousand) to generate a detailed, comprehensive map of heart chamber electrical activity. The generated detailed map may then serve as the basis for deciding on a therapeutic course of action, for example, tissue ablation as described herein, to alter the propagation of the heart's electrical activity and to restore normal heart rhythm.

Further, cardiac mapping can be generated based on detection of intracardiac electrical potential fields (e.g., which is an example of IC ECG data and/or bipolar intracardiac reference signals). A non-contact technique to simultaneously acquire a large amount of cardiac electrical information may be implemented. For example, a catheter type having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes). As another more specific example, the catheter may include other multi-spline catheters, such as five soft flexible branches, eight radial splines, or a parallel splined pancake turner type (e.g., any of which may have a total of 42 electrodes).

As example of electrical or cardiac mapping, an electrophysiological cardiac mapping system and technique based on a non-contact and non-expanded multi-electrode catheter (e.g., the catheter 110, such as a multi-spline catheter described herein) can be implemented. ECGs may be obtained with one or more catheters 110 having multiple electrodes (e.g., such as between 42 to 122 electrodes). According to this implementation, knowledge of the relative geometry of the probe and the endocardium can be obtained by an independent imaging modality, such as transesophageal echocardiography. After the independent imaging, non-contact electrodes may be used to measure cardiac surface potentials and construct maps therefrom (e.g., in some cases using bipolar intracardiac reference signals). This technique can include the following steps (after the independent imaging step): (a) measuring electrical potentials with a plurality of electrodes disposed on a probe positioned in the heart 120; (b) determining the geometric relationship of the probe surface and the endocardial surface and/or other reference; (c) generating a matrix of coefficients representing the geometric relationship of the probe surface and the endocardial surface; and (d) determining endocardial potentials based on the electrode potentials and the matrix of coefficients.

As another example of electrical or cardiac mapping, a technique and apparatus for mapping the electrical potential distribution of a heart chamber can be implemented. An intra-cardiac multi-electrode mapping catheter assembly can be inserted into the heart 120. The mapping catheter (e.g., the catheter 110) assembly can include a multi-electrode array with one or more integral reference electrodes (e.g., one or the electrodes 111) or a companion reference catheter.

According to one or more embodiments, the electrodes may be deployed in the form of a substantially spherical array, which may be spatially referenced to a point on the endocardial surface by the reference electrode or by the reference catheter this is brought into contact with the endocardial surface. The preferred electrode array catheter may carry a number of individual electrode sites (e.g., at least 24). Additionally, this example technique may be implemented with knowledge of the location of each of the electrode sites on the array, as well as knowledge of the cardiac geometry. These locations are preferably determined by a technique of impedance plethysmography.

In view of electrical or cardiac mapping and according to another example, the catheter 110 can be a heart mapping catheter assembly that may include an electrode array defining a number of electrode sites. The heart mapping catheter assembly can also include a lumen to accept a reference catheter having a distal tip electrode assembly that may be used to probe the heart wall. The map heart mapping catheter assembly can include a braid of insulated wires (e.g., having 24 to 64 wires in the braid), and each of the wires may be used to form electrode sites. The heart mapping catheter assembly may be readily positionable in the heart 120 to be used to acquire electrical activity information from a first set of non-contact electrode sites and/or a second set of in-contact electrode sites.

Further, according to another example, the catheter 110 that can implement mapping electrophysiological activity within the heart can include a distal tip that is adapted for delivery of a stimulating pulse for pacing the heart or an ablative electrode for ablating tissue in contact with the tip. This catheter 110 can further include at least one pair of orthogonal electrodes to generate a difference signal indicative of the local cardiac electrical activity adjacent the orthogonal electrodes.

As noted herein, the system 100 can be utilized to detect, diagnose, and/or treat cardiac conditions. In example operation, a process for measuring electrophysiologic data in a heart chamber may be implemented by the system 100. The process may include, in part, positioning a set of active and passive electrodes into the heart 120, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

As another example operation, cardiac mapping may be implemented by the system 100 using one or more ultrasound transducers. The ultrasound transducers may be inserted into a patient's heart 120 and may collect a plurality of ultrasound slices (e.g., two dimensional or three-dimensional slices) at various locations and orientations within the heart 120. The location and orientation of a given ultrasound transducer may be known and the collected ultrasound slices may be stored such that they can be displayed at a later time. One or more ultrasound slices corresponding to the position of the probe 105 (e.g., a treatment catheter shown as catheter 110) at the later time may be displayed and the probe 105 may be overlaid onto the one or more ultrasound slices.

In view of the system 100, it is noted that cardiac arrhythmias, including atrial arrhythmias, may be of a multiwavelet reentrant type, characterized by multiple asynchronous loops of electrical impulses that are scattered about the atrial chamber and are often self-propagating (e.g., another example of the IC ECG data). Alternatively, or in addition to the multiwavelet reentrant type, cardiac arrhythmias may also have a focal origin, such as when an isolated region of tissue in an atrium fires autonomously in a rapid, repetitive fashion (e.g., another example of the IC ECG data). Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

For example, aFib occurs when the normal electrical impulses (e.g., another example of the IC ECG data) generated by the sinoatrial node are overwhelmed by disorganized electrical impulses (e.g., signal interference) that originate in the atria veins and PVs causing irregular impulses to be conducted to the ventricles. An irregular heartbeat results and may last from minutes to weeks, or even years. aFib is often a chronic condition that leads to a small increase in the risk of death often due to strokes. A line of treatment for aFib is medication that either slows the heart rate or revert the heart rhythm back to normal. Additionally, persons with aFib are often given anticoagulants to protect them from the risk of stroke. The use of such anticoagulants comes with its own risk of internal bleeding. In some patients, medication is not sufficient and their aFib is deemed to be drug-refractory, i.e., untreatable with standard pharmacological interventions. Synchronized electrical cardioversion may also be used to convert aFib to a normal heart rhythm. Alternatively, aFib patients are treated by catheter ablation.

A catheter ablation-based treatment may include mapping the electrical properties of heart tissue, especially the endocardium and the heart volume, and selectively ablating cardiac tissue by application of energy. Electrical or cardiac mapping (e.g., implemented by any electrophysiological cardiac mapping system and technique described herein) includes creating a map of electrical potentials (e.g., a voltage map) of the wave propagation along the heart tissue or a map of arrival times (e.g., a LAT map) to various tissue located points. Electrical or cardiac mapping (e.g., a cardiac map) may be used for detecting local heart tissue dysfunction. Ablations, such as those based on cardiac mapping, can cease or modify the propagation of unwanted electrical signals from one portion of the heart 120 to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. Another example of an energy delivery technique includes irreversible electroporation (IRE), which provides high electric fields that damage cell membranes. In a two-step procedure (e.g., mapping followed by ablation) electrical activity at points within the heart 120 is typically sensed and measured by advancing the catheter 110 containing one or more electrical sensors (e.g., electrodes 111) into the heart 120 and obtaining/acquiring data at a multiplicity of points (e.g., as biometric data generally, or as ECG data specifically). This ECG data is then utilized to select the endocardial target areas, at which ablation is to be performed.

Cardiac ablation and other cardiac electrophysiological procedures have become increasingly complex as clinicians treat challenging conditions such as atrial fibrillation and ventricular tachycardia. The treatment of complex arrhythmias can now rely on the use of three-dimensional (3D) mapping systems to reconstruct the anatomy of the heart chamber of interest. In this regard, the mapping engine 101 employed by the system 100 herein manipulates and evaluates the biometric data generally, or the ECG data specifically, to produce improved tissue data that enables more accurate diagnosis, images, scans, and/or maps for treating an abnormal heartbeat or arrhythmia. For example, cardiologists rely upon software, such as the Complex Fractionated Atrial Electrograms (CFAE) module of the CARTO® 3 3D mapping system, produced by Biosense Webster, Inc. (Diamond Bar, Calif.), to generate and analyze ECG data. The mapping engine 101 of the system 100 enhances this software to generate and analyze the improved biometric data, which further provide multiple pieces of information regarding electrophysiological properties of the heart 120 (including the scar tissue) that represent cardiac substrates (anatomical and functional) of aFib.

Accordingly, the system 100 can implement a 3D mapping system, such as CARTO® 3 3D mapping system, to localize the potential arrhythmogenic substrate of the cardiomyopathy in terms of abnormal ECG detection. The substrate linked to these cardiac conditions is related to the presence of fragmented and prolonged ECGs in the endocardial and/or epicardial layers of the ventricular chambers (right and left). For instance, areas of low or medium voltage may exhibit ECG fragmentation and prolonged activities. Further, during sinus rhythm, areas of low or medium voltage may corresponds to a critical isthmus identified during sustained and organized ventricular arrhythmias (e.g., applies to non-tolerated ventricular tachycardias, as well as in the atria). In general, abnormal tissue is characterized by low-voltage ECGs. However, initial clinical experience in endo-epicardial mapping indicates that areas of low-voltage are not always present as the sole arrhythmogenic mechanism in such patients. In fact, areas of low or medium voltage may exhibit ECG fragmentation and prolonged activities during sinus rhythm, which corresponds to the critical isthmus identified during sustained and organized ventricular arrhythmias, e.g., applies only to non-tolerated ventricular tachycardias. Moreover, in many cases, ECG fragmentation and prolonged activities are observed in the regions showing a normal or near-normal voltage amplitude (>1-1.5 mV). Although the latter areas may be evaluated according to the voltage amplitude, they cannot be considered as normal according to the intracardiac signal, thus representing a true arrhythmogenic substrate. The 3D mapping may be able to localize the arrhythmogenic substrate on the endocardial and/or epicardial layer of the right/left ventricle, which may vary in distribution according to the extension of the main disease.

As another example operation, cardiac mapping may be implemented by the system 100 using one or more multiple-electrode catheters (e.g., the catheter 110). Multiple-electrode catheters are used to stimulate and map electrical activity in the heart 120 and to ablate sites of aberrant electrical activity. In use, the multiple-electrode catheter is inserted into a major vein or artery, e.g., femoral vein, and then guided into the chamber of the heart 120 of concern. A typical ablation procedure involves the insertion of the catheter 110 having at least one electrode 111 at its distal end, into a heart chamber. A reference electrode is provided, taped to the skin of the patient or by means of a second catheter that is positioned in or near the heart or selected from one or the other electrodes 111 of the catheter 110. Radio frequency (RF) current is applied to a tip electrode 111 of the ablating catheter 110, and current flows through the media that surrounds it (e.g., blood and tissue) toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the tip electrode 111 also occurs as a result of conduction from the heated tissue to the electrode itself. If the electrode temperature becomes sufficiently high, possibly above 60 degrees Celsius, a thin transparent coating of dehydrated blood protein can form on the surface of the electrode 111. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs, and the catheter 110 must be removed from the body and the tip electrode 111 cleaned.

Figure 2:
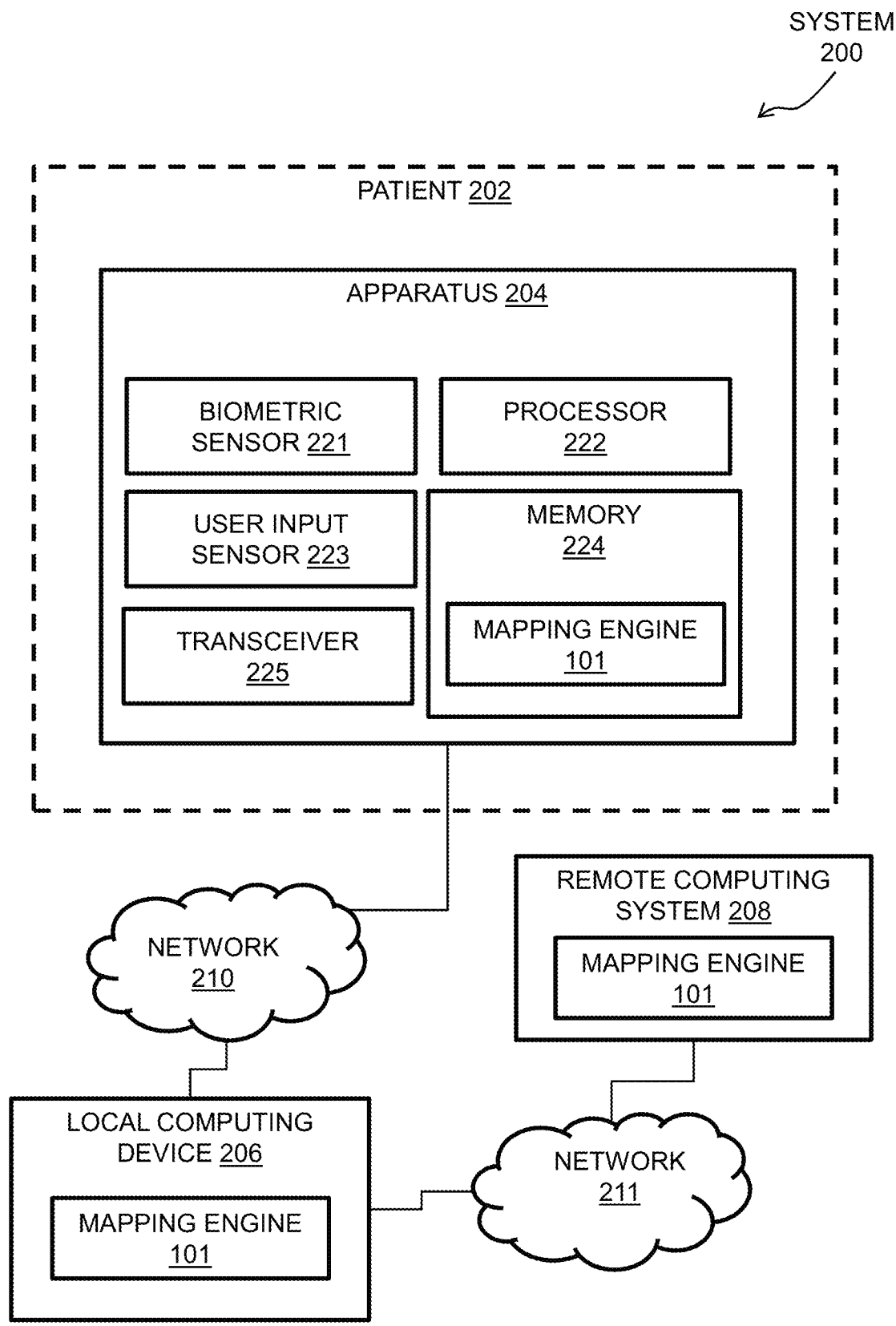
FIG. 2 illustrates a block diagram of an example system for signal and correction processing for anatomical structure mapping data according to one or more embodiments.

Turning now to FIG. 2, a diagram of a system 200 in which one or more features of the disclosure subject matter can be implemented is illustrated according to one or more embodiments. The system 200 includes, in relation to a patient 202 (e.g., an example of the patient 125 of FIG. 1), an apparatus 204, a local computing device 206, a remote computing system 208, a first network 210, and a second network 211. Further, the apparatus 204 can include a biometric sensor 221 (e.g., an example of the catheter 110 of FIG. 1), a processor 222, a user input (UI) sensor 223, a memory 224, and a transceiver 225. Note that the mapping engine 101 of FIG. 1 is reused in FIG. 2 for ease of explanation and brevity.

According to an embodiment, the apparatus 204 can be an example of the system 100 of FIG. 1, where the apparatus 204 can include both components that are internal to the patient and components that are external to the patient. According to an embodiment, the apparatus 204 can be an apparatus that is external to the patient 202 that includes an attachable patch (e.g., that attaches to a patient's skin). According to another embodiment, the apparatus 204 can be internal to a body of the patient 202 (e.g., subcutaneously implantable), where the apparatus 204 can be inserted into the patient 202 via any applicable manner including orally injecting, surgical insertion via a vein or artery, an endoscopic procedure, or a lap aroscopic procedure. According to an embodiment, while a single apparatus 204 is shown in FIG. 2, example systems may include a plurality of apparatuses.

Accordingly, the apparatus 204, the local computing device 206, and/or the remote computing system 208 can be programed to execute computer instructions with respect the mapping engine 101. As an example, the memory 223 stores these instructions for execution by the processor 222 so that the apparatus 204 can receive and process the biometric data via the biometric sensor 201. IN this way, the processor 22 and the memory 223 are representative of processors and memories of the local computing device 206 and/or the remote computing system 208.

The apparatus 204, local computing device 206, and/or the remote computing system 208 can be any combination of software and/or hardware that individually or collectively store, execute, and implement the mapping engine 101 and functions thereof. Further, the apparatus 204, local computing device 206, and/or the remote computing system 208 can be an electronic, computer framework comprising and/or employing any number and combination of computing device and networks utilizing various communication technologies, as described herein. The apparatus 204, local computing device 206, and/or the remote computing system 208 can be easily scalable, extensible, and modular, with the ability to change to different services or reconfigure some features independently of others.

The networks 210 and 211 can be a wired network, a wireless network, or include one or more wired and wireless networks. According to an embodiment, the network 210 is an example of a short-range network (e.g., local area network (LAN), or personal area network (PAN)). Information can be sent, via the network 210, between the apparatus 204 and the local computing device 206 using any one of various short-range wireless communication protocols, such as Bluetooth, Wi-Fi, Zigbee, Z-Wave, near field communications (NFC), ultra-band, Zigbee, or infrared (IR). Further, the network 211 is an example of one or more of an Intranet, a local area network (LAN), a wide area network (WAN), a metropolitan area network (MAN), a direct connection or series of connections, a cellular telephone network, or any other network or medium capable of facilitating communication between the local computing device 206 and the remote computing system 208. Information can be sent, via the network 211, using any one of various long-range wireless communication protocols (e.g., TCP/IP, HTTP, 3G, 4G/LTE, or 5G/New Radio). Note that for either network 210 and 211 wired connections can be implemented using Ethernet, Universal Serial Bus (USB), RJ-11 or any other wired connection and wireless connections can be implemented using Wi-Fi, WiMAX, and Bluetooth, infrared, cellular networks, satellite or any other wireless connection methodology.

In operation, the apparatus 204 can continually or periodically obtain, monitor, store, process, and communicate via network 210 the biometric data associated with the patient 202. Further, the apparatus 204, local computing device 206, and/or the remote computing system 208 are in communication through the networks 210 and 211 (e.g., the local computing device 206 can be configured as a gateway between the apparatus 204 and the remote computing system 208). For instance, the apparatus 204 can be an example of the system 100 of FIG. 1 configured to communicate with the local computing device 206 via the network 210. The local computing device 206 can be, for example, a stationary/standalone device, a base station, a desktop/laptop computer, a smart phone, a smartwatch, a tablet, or other device configured to communicate with other devices via networks 211 and 210. The remote computing system 208, implemented as a physical server on or connected to the network 211 or as a virtual server in a public cloud computing provider (e.g., Amazon Web Services (AWS)®) of the network 211, can be configured to communicate with the local computing device 206 via the network 211. Thus, the biometric data associated with the patient 202 can be communicated throughout the system 200.

Elements of the apparatus 204 are now described. The biometric sensor 221 may include, for example, one or more transducers configured to convert one or more environmental conditions into an electrical signal, such that different types of biometric data are observed/obtained/acquired. For example, the biometric sensor 221 can include one or more of an electrode (e.g., the electrode 111 of FIG. 1), a temperature sensor (e.g., thermocouple), a blood pressure sensor, a blood glucose sensor, a blood oxygen sensor, a pH sensor, an accelerometer, and a microphone.

The processor 222, in executing the mapping engine 101, can be configured to receive, process, and manage the biometric data acquired by the biometric sensor 221, and communicate the biometric data to the memory 224 for storage and/or across the network 210 via the transceiver 225. Biometric data from one or more other apparatuses 204 can also be received by the processor 222 through the transceiver 225. Also, as described in more detail herein, the processor 222 may be configured to respond selectively to different tapping patterns (e.g., a single tap or a double tap) received from the UI sensor 223, such that different tasks of a patch (e.g., acquisition, storing, or transmission of data) can be activated based on the detected pattern. In some embodiments, the processor 222 can generate audible feedback with respect to detecting a gesture.

The UI sensor 223 includes, for example, a piezoelectric sensor or a capacitive sensor configured to receive a user input, such as a tapping or touching. For example, the UI sensor 223 can be controlled to implement a capacitive coupling, in response to tapping or touching a surface of the apparatus 204 by the patient 202. Gesture recognition may be implemented via any one of various capacitive types, such as resistive capacitive, surface capacitive, projected capacitive, surface acoustic wave, piezoelectric and infrared touching. Capacitive sensors may be disposed at a small area or over a length of the surface, such that the tapping or touching of the surface activates the monitoring device.

The memory 224 is any non-transitory tangible media, such as magnetic, optical, or electronic memory (e.g., any suitable volatile and/or non-volatile memory, such as random-access memory or a hard disk drive). The memory 224 stores the computer instructions for execution by the processor 222.

The transceiver 225 may include a separate transmitter and a separate receiver. Alternatively, the transceiver 225 may include a transmitter and receiver integrated into a single device.

In operation, the apparatus 204, utilizing the mapping engine 101, observes/obtains the biometric data of the patient 202 via the biometric sensor 221, stores the biometric data in the memory, and shares this biometric data across the system 200 via the transceiver 225. The mapping engine 101 can then utilize fuzzy logic, models, neural networks, machine learning, and/or artificial intelligence to reduce user intervention, improve scar identification, and enable discrimination between low conduction and no conduction. Generally, the mapping engine 101 provides a number of operations for assigning scar probabilities. The number of operations can include, but are not limited to, automatic tagging, time weighted LAT assignments, and discrimination of slow or non-conduction conditions.

Figure 3:
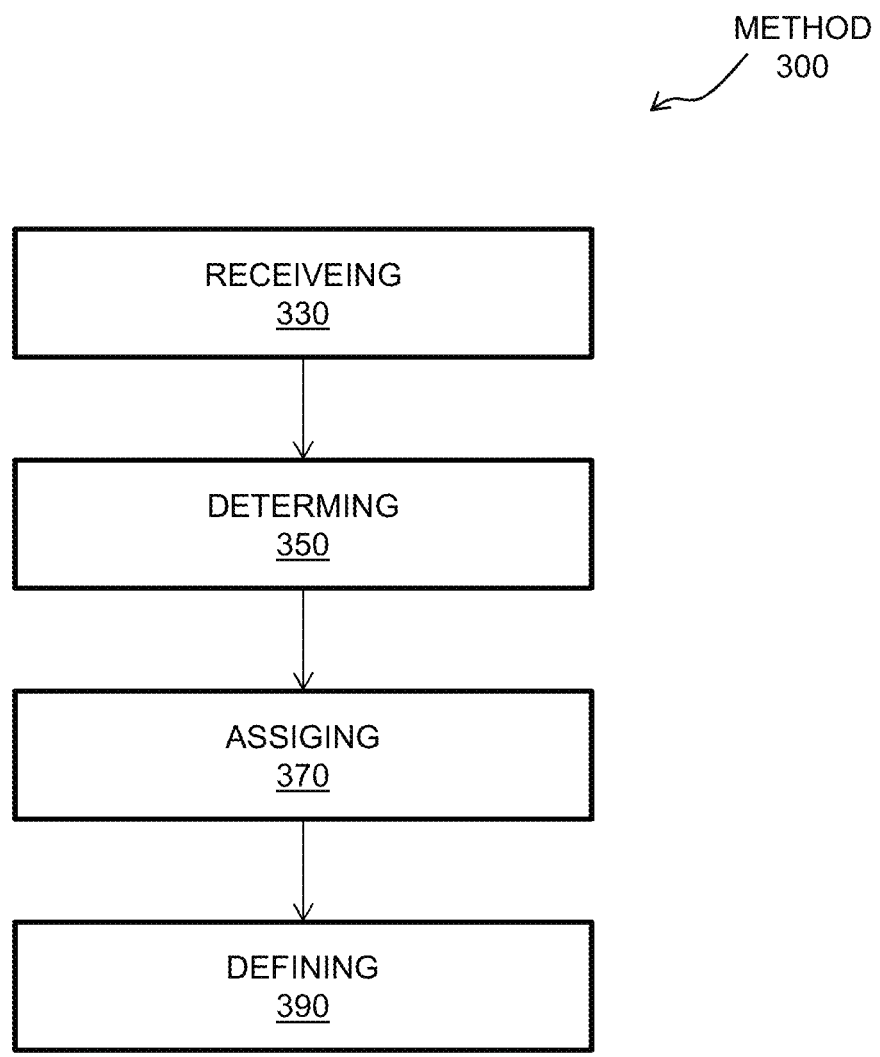
FIG. 3 illustrates an exemplary method according to one or more embodiments.
Figure 4:
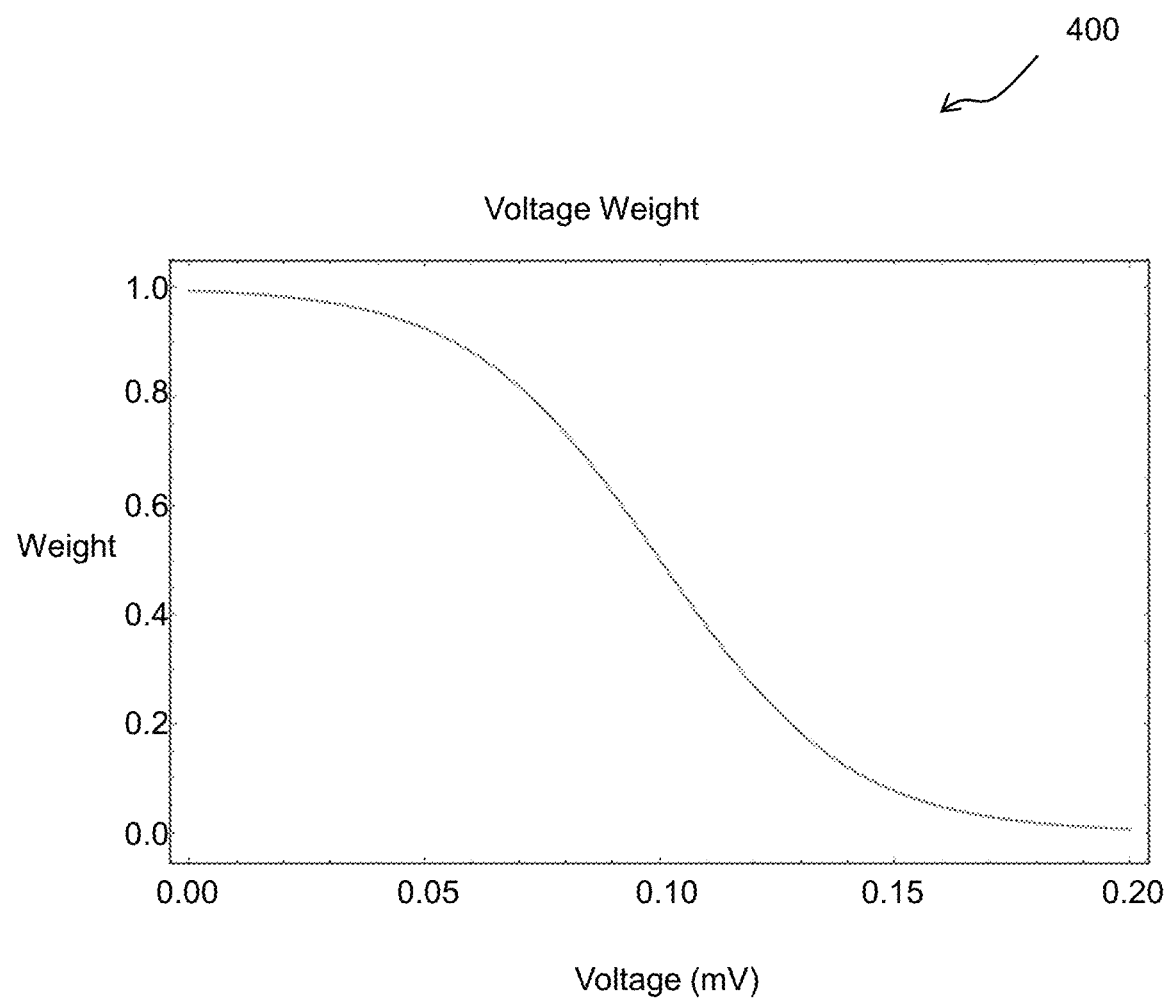
FIG. 4 illustrates graph depicting automatic scar measurement tagging according to one or more embodiments.
Figure 5:
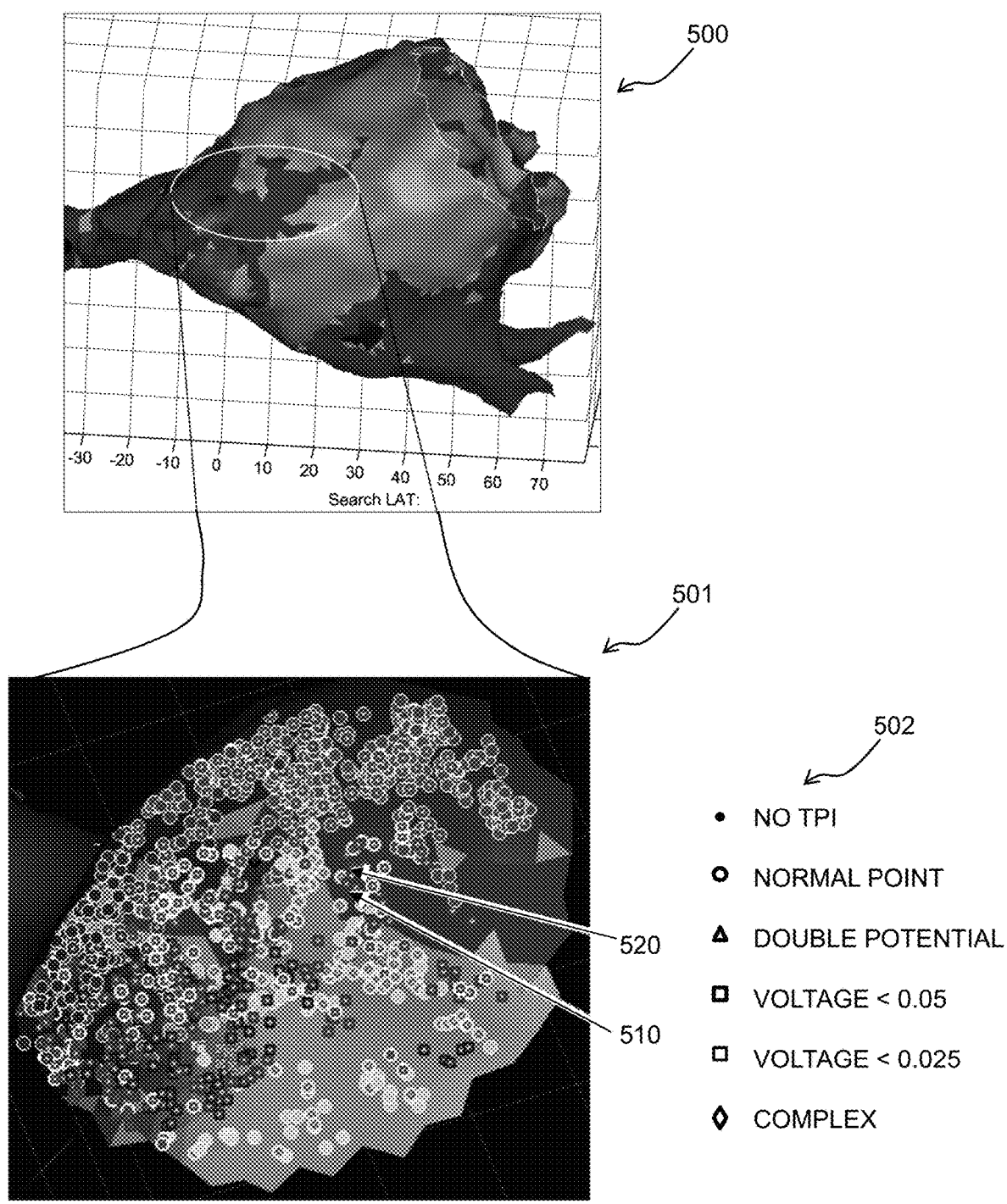
FIG. 5 illustrates example interfaces depicting automatic scar measurement tagging according to one or more embodiments.

Turning now to FIGS. 3-5, automatic tagging operations are described for the mapping engine 101.

As seen in FIG. 3, a method 300 (e.g., performed by the mapping engine 101 of FIG. 1 and/or of FIG. 2) is illustrated according to one or more exemplary embodiments. The method 300 by the mapping engine 101, in general, automatically identifies scar tissue on the heart from the electrical signals (e.g., using the notion that scar tissue blocks the heartbeat by more or less not conducting electrical signals). In turn, the method 300 by the mapping engine 101 addresses deficiencies of current coherent mapping algorithms by providing a multi-step manipulation of electrical signals that enables an improved understanding an electrophysiology with more precision.

The method begins at block 330, where the mapping engine 101 receives biometric data from at least the catheter 110. The biometric data includes electrical measurements of a patient's anatomical structure (e.g., the heart 120) and one or more references signals.

At block 350, the mapping engine 101 determines which electrical measurements of the biometric data have an indication associated therewith. This determination generates a sub-data set of electrical measurements. According to an embodiment, the indication can be a tissue proximity indicator (TPI) feature of the mapping engine 101. TPI can use an impedance-based algorithm to detect a catheter's 110 proximity to tissue, such that any real-time change in impedance in each electrode of the catheter 110 is used to decide if there is proximity to the tissue. Thus, an active TPI for a particular measurement indicates that the mapping engine 101 can recognize that the catheter 110 is in contact with the tissue.

At block 370, the mapping engine 101 assigns a scar probability to each electrical measurement of the sub-data set. The scar probability is assigned based on voltage, for example, using fuzzy logic (instead of a threshold). Fuzzy logic is a mathematical logic form in which truth values of variables can be any real number between 0 and 1. For instance, if there is low voltage on the catheter 110 at the time of acquiring the electrical measurement and there is an active TPI, then there is contact (by the catheter 110 with the tissue). In turn, the mapping engine 101 can automatically assign that this point to be a point that contributes to a scar (e.g., a scar point in general or with respect to a particular feature).

At block 390, the mapping engine 101 uses the scar probability to define scar tissue on a triangular mesh, when generating a map. The technical effects and benefits of the method 300 include reducing user intervention, improving scar identification, and enabling discrimination between low conduction and no conduction.

FIG. 4 illustrates a graph 400 depicting automatic scar measurement tagging (as implemented by the mapping engine 101). The automatic scar measurement tagging shown by the graph 400 removes the dependence on manual scar tagging by the user by assigning a scar probability based on combining a voltage for measurements with a TPI.

For example, for measurements with the TPI, the mapping engine 101 assigns scar probability based on voltage, for purposes of defining scar tissue on the triangular mesh. In this way, the mapping engine 101 uses the catheter 110 to measure points, voltage at the points, and signal arrival times of the points. If a point has a very low voltage (e.g., indicating that there is scar tissue), the mapping engine 101 provide for automatic scar measurement tagging. In accordance with another embodiment, the mapping engine 101 can implement an integration scheme to define scar tissue on mesh, such as a probability of a wall face to be a scar depends on a distance to nearest scar measurement.

As seen in FIG. 5, example interfaces 500 and 501 depict automatic scar measurement tagging (as implemented by the mapping engine 101). Interface 500 is an example mapping of an overall heart map as rendered by the mapping engine 101 (e.g., a map of a heart generated by performing interpolation operations). Interface 501 is an example mapping of a selected zone as rendered by the mapping engine 101, and includes the legend 502. Measurement 510 has a low voltage and a TPI, and therefore can be tagged by the mapping engine 101 as a scar measurement (e.g., the arrow for measurement 510 points to a square with no dot in it). Measurement 520 has a low voltage without a TPI, and therefore is not tagged by the mapping engine 101 as a scar measurement (e.g., the arrow for measurement 520 points to a square with a dot in it, which means that there was no TPI indication with respect to the legend 502.

Figure 6:
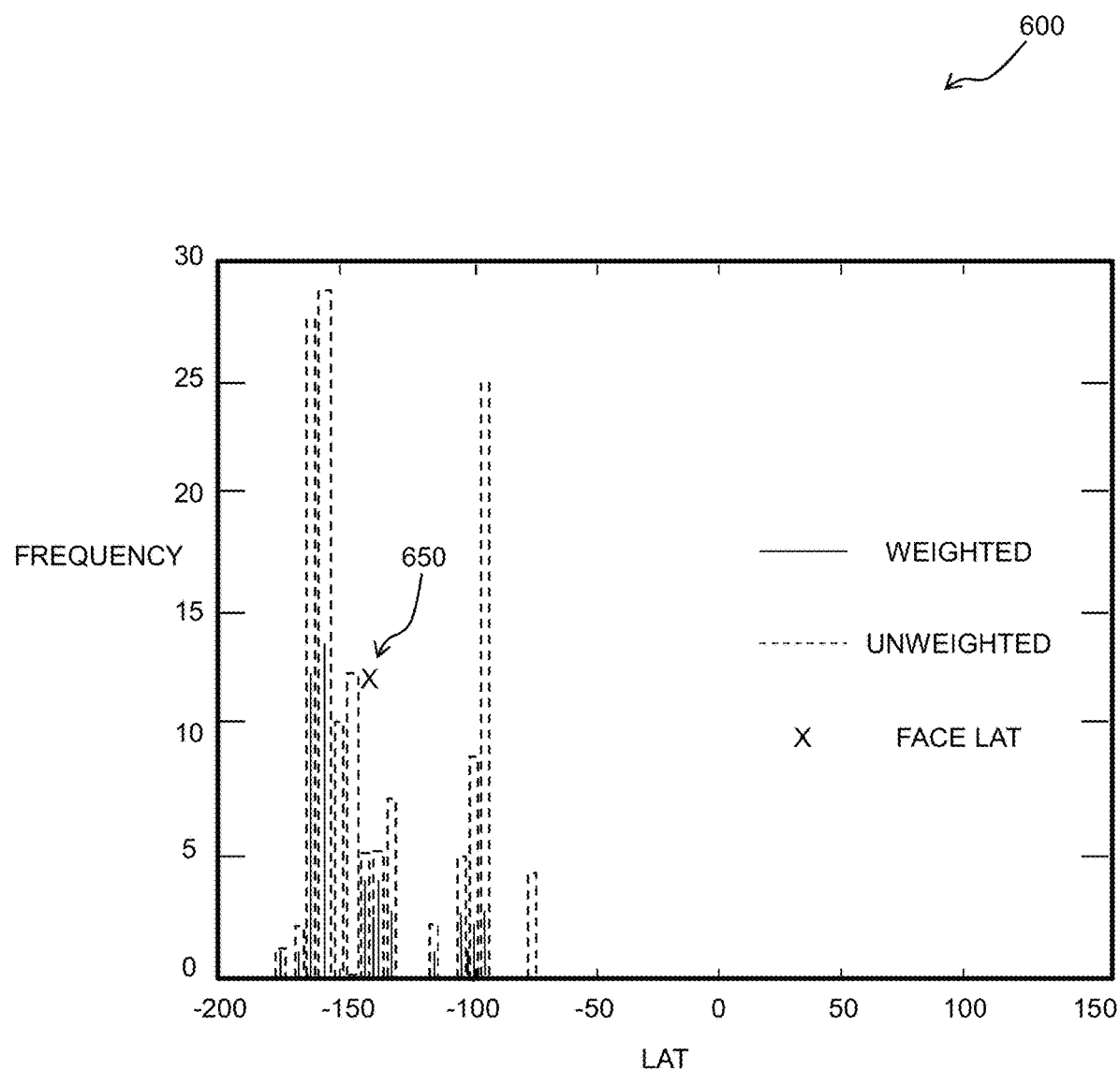
FIG. 6 illustrates example interfaces depicting automatic scar measurement tagging according to one or more embodiments.
Figure 7:
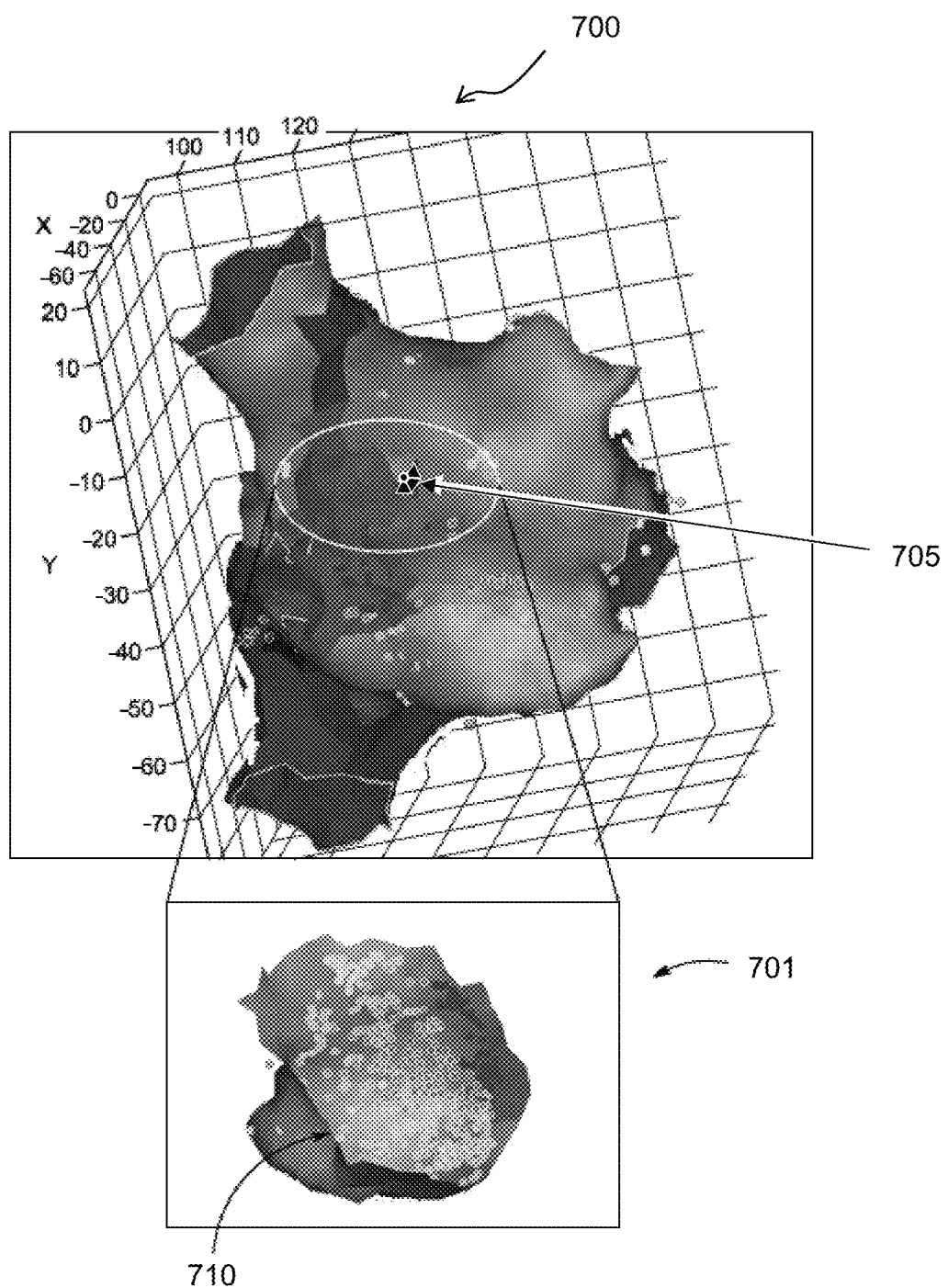
FIG. 7 illustrates graph depicting automatic scar measurement tagging according to one or more embodiments.
Figure 8:
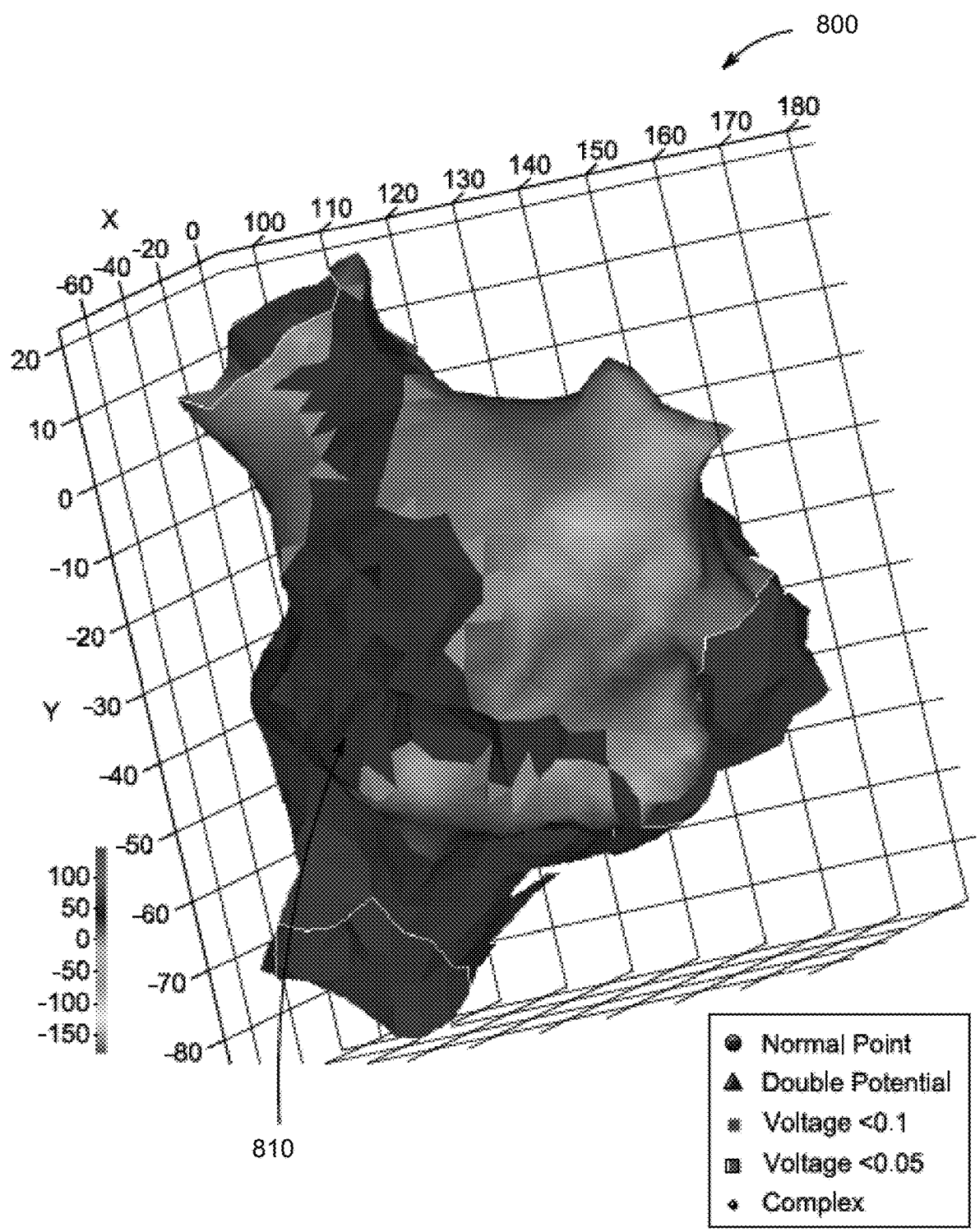
FIG. 8 illustrates an example interface depicting automatic scar measurement tagging according to one or more embodiments.

Turning now to FIGS. 6-8, the mapping engine 101 is further described with respect to time weighted LAT assignments in accordance with one or more embodiments. In general, time weighted LAT assignments include determining a duration of a time window and identifying/weighting signals within that time window with respect to normal bipolar beats and blockages.

FIG. 6 illustrates a graph 700 of frequency vs. LAT depicting a distribution of LATs of points, contributing to a frontier. A first distribution includes an unweighted LAT distribution of points contributing to LAT assignment before reweight, and a second distribution includes a weighted LAT distribution of points. Further, in the graph 600, note that each distribution has two peaks.

In view of FIG. 6, the mapping engine 101 discovers, based on signal flow from the catheter 110, that a distribution of points can be bifurcated (some associated with tissue on one side/some associated on the other side). In operation, the mapping engine 101 can perform a find a peak search of the distribution of points contributing to every triangle of the triangle mesh. When there is a bifurcation, the mapping engine 101 applies an iterative algorithm of the two peak locations so a previous iteration (e.g., a previous solution for the Lat time assigned to any particular triangle) is used to measure the peaks. As shown in FIG. 6, the weight of the points can be determined by their time difference from the face LAT of previous iteration (see a Face LAT 650 of a previous iteration), which will dampen the contribution from the smaller distribution. When there is a bifurcation, the mapping engine 101 choses only the distribution that is closer to a time of the previous iteration/solution (e.g., throws away one bump and use the other).

With respect to time weighted LAT assignments, the mapping engine 101 determines a time window and identifies/weights signals within that time window with respect to normal bipolar beats and blockages. According to one or more embodiments, the time weighted LAT assignments operations overcome the problems of current coherent mapping algorithms.

Conventionally, the physician who is operating the system of the current coherent mapping algorithms must determine which time period to analyze. Thus, when an electroanatomical map is acquired, a clinician chooses a signal to be a reference signal. This reference signal can be from an electrode in a catheter placed in an anatomical structure (e.g., the coronary sinus) or some time derived from a combination of signals. A time period surrounding this reference signal can be defined by the clinician. Signals from the catheter within a portion of the anatomical structure (e.g., a chamber) are assigned negative LAT values if they arrive before the reference signal and positive LAT values if they arrive after the reference signal (e.g., some signals come before a given reference time and other signals come after). There may be situations where the clinician defines the time period as too small, and a fractionated signal is not be fully included (e.g., and thereby not detected). There may also be situations where the clinician defines the time period as too long, and a same signal is included twice. In some cases, these time period sizing mistakes may be less due to user error and more due to small variations of a time between reference signals.

According to an embodiment, the mapping engine 101 automatically defines a time window to be a time span (e.g., a duration) between two reference signal annotations, so as to include any fractionated signal and exclude duplicate signals. In this way, the mapping engine 101 can be configured to automatically select a (e.g., largest or smallest) time window. According to another embodiment, the mapping engine 101 automatically selects the time window based on an input from the physician 115. For instance, the mapping engine 101 takes two known reference signals, and requires the physician 115 to choose a pre-determined window between the two reference signals (e.g., instead of having the physician take one reference point, and then choose an arbitrary duration for the window). Thus, the mapping engine 101 determines a duration of the time window, and also automatically identifies the signals that correspond to normal bipolar beats, and double-potential signals that correspond to blockages (e.g., a block).

One or more advantages, technical effects, and benefits of the mapping engine 101 can, in turn, include significantly reducing user intervention from the requirement by current coherent mapping algorithms for where physicians take one reference point and an arbitrarily chose a duration for the time period. Accordingly, the mapping engine 101 reduces physician error and artifacts by reducing user intervention.

As seen in FIG. 7, example interfaces 700 and 701 depicting automatic scar measurement tagging (as implemented by the mapping engine 101) are shown. Interface 700 is an example mapping of an overall heart map as rendered by the mapping engine. Interface 701 is an example mapping of a selected zone as rendered by the mapping engine 101. FIG. 7 illustrates how the mapping engine 101, in relation to improved scar identification (e.g., at point 705), correctly detects lines of block via time weighted LAT measurement (e.g., from FIG. 6). In the selected zone of interface 701, there is a frontier 710 between two widely separated LAT distributions. The mapping engine 101 would expect to see at, this frontier 710, a block. For instance, the mapping engine 101 can re-weight measurements with bimodal LATs, so that blocks may be detected. Note that a block refers to the notion that scar tissue prevents transmission of a heartbeat by not conducting electrical signals.

The mapping engine 101 then discovers, as the mapping is leaning to one side vs. the other, a clean break with sharp separations of times of adjacent iterations. With the sharp separation of times, the mapping engine 101 creates a line of blocks. For example, FIG. 8 illustrates an interface 800 showing a line of blocks 810. The interface 800 of FIG. 8 can be compared to the interface 700 of FIG. 7 (which does not have a line of block).

Figure 9:
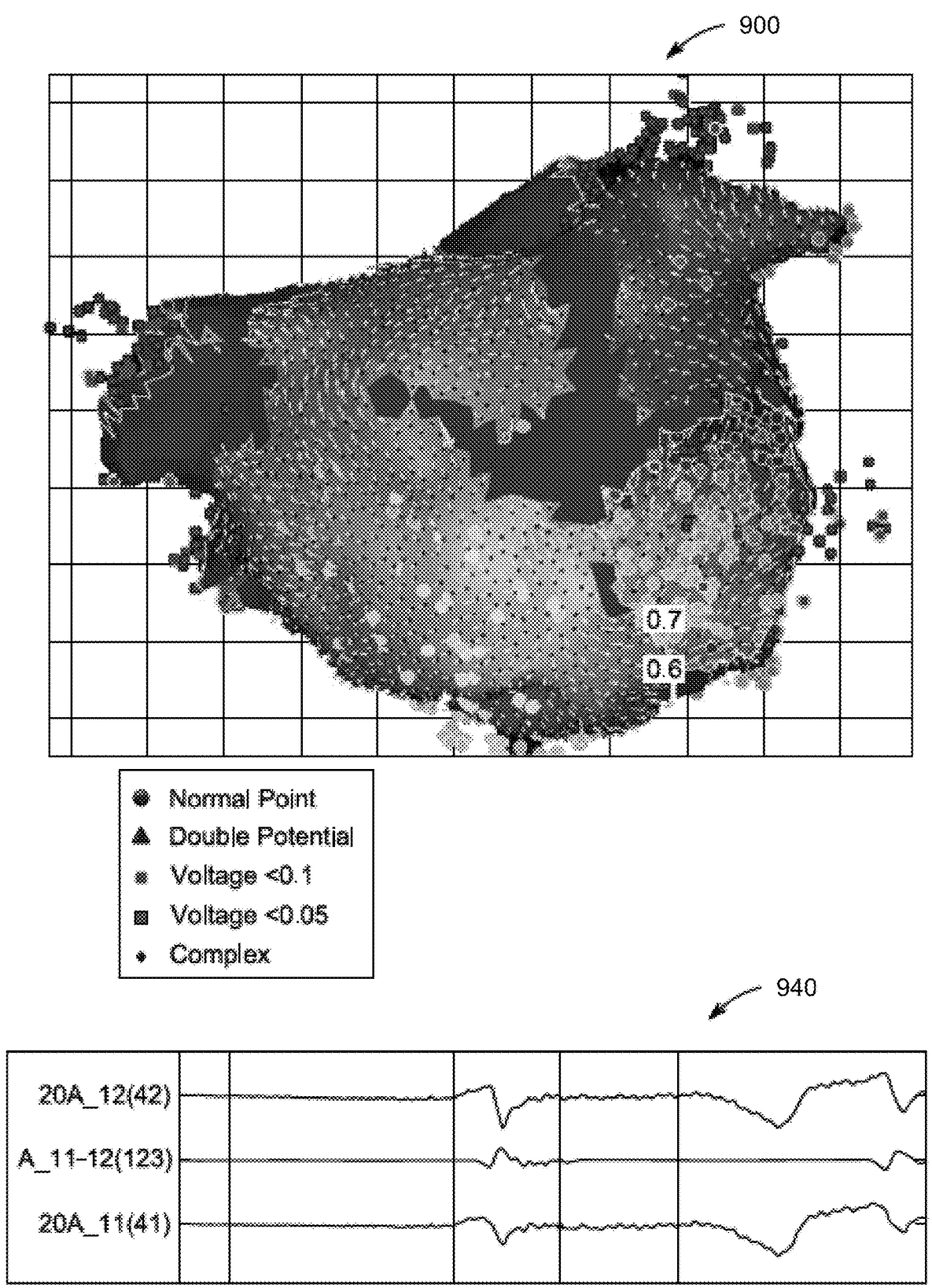
FIG. 9 illustrates an example interface and a graph according to one or more embodiments.
Figure 10:
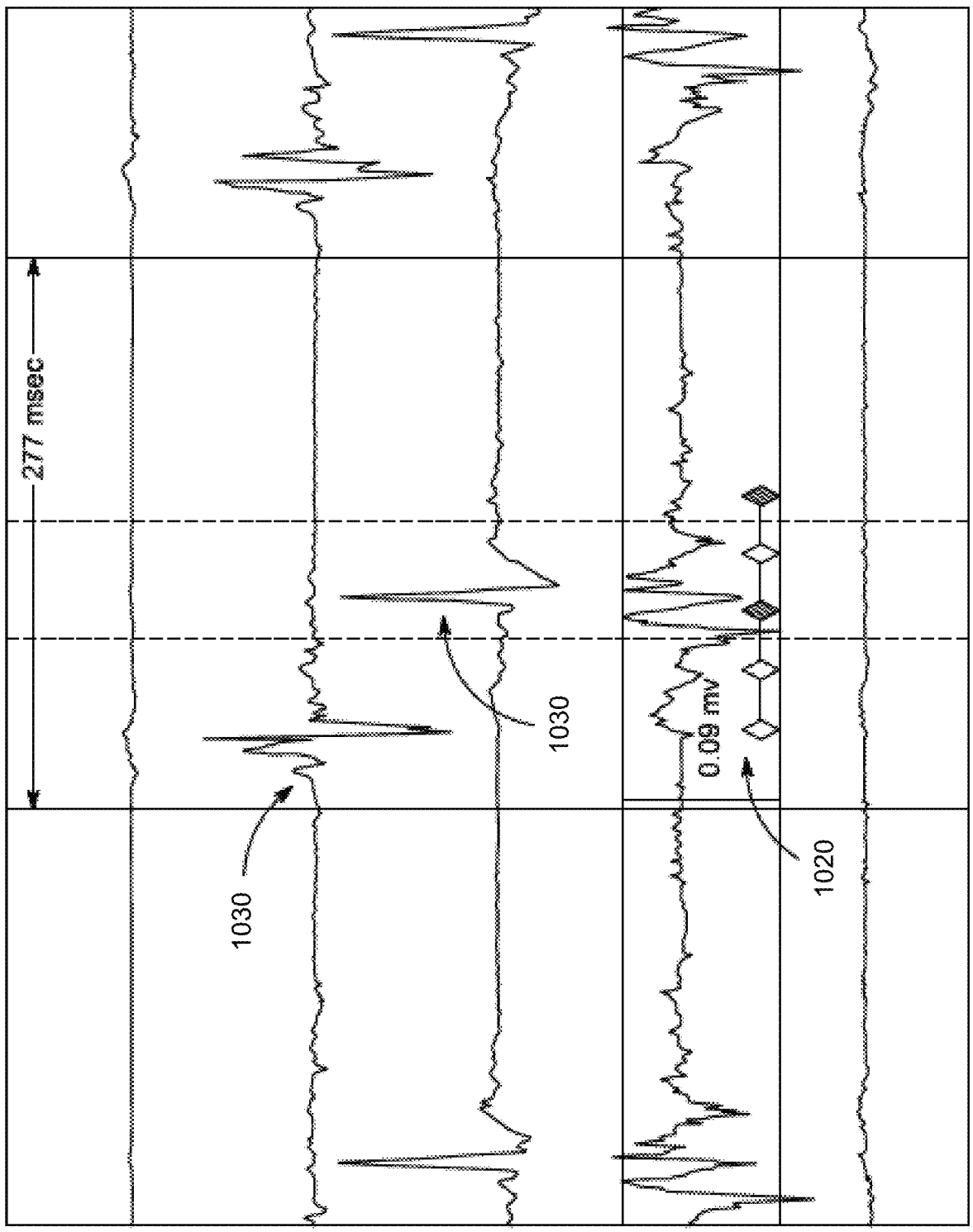
FIG. 10 illustrates a graph according to one or more embodiments.

Turning now to FIGS. 9-10, the mapping engine 101 is further described with respect to discrimination of slow or non-conduction conditions (e.g., sometimes referred to as low or no voltage conditions) in accordance with one or more embodiments. More particularly, the mapping engine 101 can determine whether a triangle (e.g., the annotation point) falls within one of three categories (e.g., normal conductivity, low conductivity, and no conductivity) with an objective to integrate all capabilities of the mapping engine 101. In this regard, the mapping engine 101 is aware that signals can actually pass through lines of block. For instance, if the catheter 110 is at a point that has an indication (e.g., the active TPI is a feature of the system) and there is low voltage on the catheter at the time of acquiring, the mapping engine 101 automatically assign this point as contributing to a scar as described here. Again, the technical benefit, in turn, is that the physician 115 is not setting the threshold themselves because the mapping engine 101 uses fuzzy logic (instead of threshold) and requires an indication of proximity. Further, the mapping system can utilize these points with respect to slow or non-conducting (SNO) zones. In this reface, a wall face of the heart 120 has probability of either normal zone or SNO zone. The mapping system 101 starts with classifying SNO zones. The mapping system 101 uses inputs from the biometric data, such as voltage, double potentials, fractionation, and velocity direction. FIG. 9 illustrates an interface 900 and a graph 940 according to one or more embodiments. The interface 900 illustrates that there is no waiting for a dedicated fractionation algorithm, as the mapping engine 101 can collect cases with manual tagged fractionation. The graph 940 illustrates these cases. At FIG. 10, a graph 1001 illustrates integrate fractionated signals according to one or more embodiments. If a triangle that was initially identified as non-conducting is near a fractionated signal 1020, the mapping engine 101 restores the continuity conditions to the triangle in the overall solution. The mapping engine 101 can further add a set of (weighted) measurement inputs at the location of the fractionated measurement, which spans the time of the fractionated signal. This may span the times of the neighboring measured signals 1030. the fractionated signals in FIG. 10 come from the atrium.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for detecting cardiac scar tissue using a catheter having a plurality of electrodes, the method comprising:
   receiving electrical signals comprising biometric data of at least a portion of a heart from the catheter having the plurality of electrodes, wherein the electrical signals are received while the catheter is positioned within the heart during a medical procedure;
   determining that a tissue proximity indicator feature associated with the portion of the heart is active based on an output of an impedance-based algorithm that detects contact of the catheter to tissue in accordance with real-time changes in impedance of the plurality of electrodes;
   assigning a scar parameter to the portion of the heart based on a voltage of the electrical signals and a distance to a nearest scar measurement among a plurality of scar measurements;
   detecting that the portion of the heart corresponds to the cardiac scar tissue when both the tissue proximity indicator feature is active and the scar parameter is indicative of scar tissue, and
   performing an operation using the catheter in accordance with the portion of the heart detected as corresponding to the cardiac scar tissue g, wherein the operation comprises at least one of an automatic tagging operation, a time weighted local activation time assignment operation, or a discrimination operation.

2. The method of claim 1, further comprising:
   determining electrical measurements of the biometric data that have the tissue proximity indicator feature associated therewith to generate a sub-data set of measurements; and
   assigning a scar probability to each measurement of the sub-data set.

3. The method of claim 2, wherein the method further comprises determining a time window and which of the electrical measurements within the time window have the tissue proximity indicator feature to generate the sub-data set.

4. The method of claim 2, wherein the tissue proximity indicator feature identifies contact by the catheter with the portion of an anatomical structure.

5. The method of claim 2, wherein the scar probability is assigned using fuzzy logic.

6. The method of claim 2, wherein the scar probability is used to define scar tissue on a triangular mesh.

7. The method of claim 2, wherein the biometric data includes one or more references signals and the electrical measurements.

8. The method of claim 1, wherein selected signals comprise a time that is closer to a local activation time assigned to a triangle in a previous iteration.

9. The method of claim 1, wherein the discrimination operation comprises determining whether an annotation point of the biometric data falls within a normal conductivity, a low conductivity, or a no conductivity.

10. The method of claim 1, wherein the impedance in each electrode of the catheter identifies a resistance measurement at a given location in an anatomical structure.

11. The method of claim 1, wherein the electrical signals are received during an ablation procedure.

12. A system for detecting cardiac scar tissue, the system comprising:
- a catheter that includes a plurality of electrodes;
- a memory that stores processor executable code; and
- one or more processors communicatively coupled to the memory, wherein the one or more processors are collectively configured to:
- receive electrical signals comprising biometric data of at least a portion of a heart from the plurality of electrodes, wherein the electrical signals are received while the catheter is positioned within the heart during a medical procedure;
- determine that a tissue proximity indicator feature associated with the portion of the heart is active based on an output of an impedance-based algorithm that detects contact of the catheter to tissue in accordance with real-time changes in impedance of the plurality of electrodes;
- assign a scar parameter to the portion of the heart based on a voltage of the electrical signals and a distance to a nearest scar measurement among a plurality of scar measurements;
- detect that the portion of the heart corresponds to the cardiac scar tissue when both the tissue proximity indicator feature is active and the scar parameter is indicative of scar tissue, and
- perform an operation in accordance with the portion of the heart detected as corresponding to the cardiac scar tissue, wherein the operation comprises at least one of an automatic tagging operation, a time weighted local activation time assignment operation, or a discrimination operation.

13. The system of claim 12, wherein the one or more processors are further collectively configured to
- determine electrical measurements of the biometric data that have the tissue proximity indicator feature associated therewith to generate a sub-data set of measurements; and
- assign a scar probability to each measurement of the sub-data set.

14. The system of claim 13, wherein the one or more processors are further collectively configured to:
- determine a time window and which of the electrical measurements within the time window have the tissue proximity indicator feature to generate the sub-data set.

15. The system of claim 13, wherein the tissue proximity indicator feature identifies contact by the catheter with the portion of an anatomical structure.

* * * * *

UNITED STATES PATENT AND TRADEMARK OFFICE
CERTIFICATE OF CORRECTION

PATENT NO. : 12,350,073 B2  
APPLICATION NO. : 17/116854  
DATED : July 8, 2025  
INVENTOR(S) : Avram Dan Montag et al.

Page 1 of 1

It is certified that error appears in the above-identified patent and that said Letters Patent is hereby corrected as shown below:

In the Specification
In Column 3, Line 27, delete "each" and insert -- that each --, therefor.
In Column 5, Line 24, delete "treatment" and insert -- treat --, therefor.
In Column 6, Line 23, delete "respect" and insert -- respect to --, therefor.
In Column 10, Line 52, delete "atria veins" and insert -- atrial veins --, therefor.
In Column 13, Line 17, delete "lap aroscopic" and insert -- laparoscopic --, therefor.
In Column 13, Line 23, delete "the" and insert -- to the --, therefor.
In Column 14, Line 23, delete "(AWS)®)" and insert -- (AWS) ®) --, therefor.
In Column 16, Line 38, delete "(e.g.," and insert -- e.g., --, therefor.
In Column 18, Line 49, delete "integrate" and insert -- integrated --, therefor.
In Column 18, Line 58, delete "the fractionated" and insert -- The fractionated --, therefor.
In Column 19, Line 28, delete "wire" and insert -- wire. --, therefor.

In the Claims
In Column 20, Line 24, in Claim 1, delete "tissue, and" and insert -- tissue; and --, therefor.
In Column 20, Line 27, in Claim 1, delete "tissue g," and insert -- tissue, --, therefor.
In Column 22, Line 2, in Claim 12, delete "tissue, and" and insert -- tissue; and --, therefor.
In Column 22, Line 10, in Claim 13, delete "configured to" and insert -- configured to: --, therefor.

Signed and Sealed this  
Second Day of September, 2025

Coke Morgan Stewart  
*Acting Director of the United States Patent and Trademark Office*